United States Patent [19]

Hiestand et al.

[11] Patent Number: 4,957,003
[45] Date of Patent: Sep. 18, 1990

[54] SLOW STRAIN RATE SHEAR STRENGTH TESTER FOR COMPACT

[75] Inventors: Everett N. Hiestand, Galesburg; Stephen Balog, Kalamazoo; David D. Gleason, Oshtemo, all of Mich.

[73] Assignee: The Upjohn Company, Kalamazoo, Mich.

[21] Appl. No.: 405,459

[22] Filed: Sep. 8, 1989

[51] Int. Cl.$^5$ ............................................... G01N 3/40
[52] U.S. Cl. ............................................ 73/818; 73/78
[58] Field of Search ................... 73/78, 821, 818, 841, 73/842

[56] References Cited

U.S. PATENT DOCUMENTS 4,393,717  7/1983  Mason et al. ..................... 73/821
4,542,646  9/1985  Smith et al. ....................... 73/78

OTHER PUBLICATIONS

"Indices of Tableting Performance," E. N. Hiestand and D. P. Smith, The Upjohn Company, 1983, (15 pages).

Primary Examiner—Jerry W. Myracle
Attorney, Agent, or Firm—Flynn, Thiel, Boutell & Tanis

[57] ABSTRACT

A slow strain rate shear strength tester for a tablet of compressed pharmaceutical powders, which apparatus includes a ram assembly having a reciprocal ram horizontally slidably supported on a housing. The ram projects outwardly of the housing and mounts a compression member on the free end thereof. A head arrangement is removably mounted on a pair of brackets which project from the end of the housing. The head arrangement has opposed holding members which cooperate to define a notch for accommodating a compact therein in position for compression by the ram.

7 Claims, 7 Drawing Sheets

SLOW STRAIN RATE SHEAR STRENGTH TESTER FOR COMPACT

FIELD OF THE INVENTION

This invention relates to an improved apparatus for measuring the slow strain rate shear strength of a compact or tablet of pharmaceutical powders.

BACKGROUND OF THE INVENTION

In the pharmaceutical industry, it is important to know the parameters which characterize the tableting properties of powders which are compressed to form tablets used for human and animal consumption. It is desirable to have a method of quantitatively evaluating the tableting characteristics of a powder before it is mixed with other materials so as to permit detection and rejection of lots that, if used, would introduce problems such as capping or excessive friability. Such methods should also be useful to assist in formulating new chemical entities. By being able to initially define what tableting indices are critical, and then by being able to experimentally measure such indices based on compacts formed from test samples, the need for formulation of large samples and the control and predictability of the tableting performance can be much more predictability controlled and achieved.

It is believed that the bonding index of the powder is probably the most important parameter, and it has been further determined that the bonding index itself involves two tableting indices, one being referred to as the best case bonding index, and the other being referred to as the worst case index. The difference between the best case and worst case bonding indices indicate whether the material is viscoelastic. If the final formulation of the powder is viscoelastic, then it will be sensitive to the rate that the tableting machine is run, that is, to the strain rate. However, viscoelasticity promotes stronger bonding. Thus, a quantitative evaluation of the difference between these best case and worst case bonding indices is highly desirable.

An evaluation of the bonding index involves application of a compressive load to a surface of a compact (i.e., a rather large blocklike tablet of compressed powder). This involves creation of a partial spherical indentation into the surface of the compact to permit a hardness value to be determined.

To experimentally determine the worst case bonding index, it is typical to use a procedure whereby a steel sphere or ball is bounced off a surface of the compact, whereby the steel ball creates a partial spherical depression in the compact. The steel ball, upon impact against the surface of the compact, imposes a compressive load on the compact, and the mean pressure under the ball is an indication of the shear strength of the compact under compressive load. This hence permits determination of the worst case bonding index. A desirable pendulum-type impact tester for this purpose is illustrated and described in co-pending application Ser. No. 07/197,841, filed on May 24, 1988, now U.S. Pat. No. 4,885,933.

To obtain a hardness which corresponds to the best case bonding index, however, requires use of a procedure which creates a very slow effective strain rate when a compressive load is imposed on the compact, such as by means of a sphere. Hence, the present invention relates to an improved apparatus which is designed specifically for permitting slow strain rate shear strength testing of a compact formed of pharmaceutical powders or particulate materials, which apparatus permits a hardness determination by using a very slow effective strain rate so as to permit determination of the best case bonding index of the material.

More specifically, this invention relates to an improved slow strain rate shear strength tester for a compact, as aforesaid, which tester involves a ram structure which is capable of pushing a ball into the surface of the compact while allowing a significant dwell time during the compression to obtain a partially or a completely relaxed hardness value due to viscoelastic effects.

In the improved tester of this invention, the apparatus is provided with an improved compact or tablet holding head arrangement which can be readily mounted on or removed from the apparatus, and which head arrangement itself greatly facilitates the mounting on or removal of a compact when testing is to be carried out.

This improved tester, as aforesaid, in addition readily mounts thereon an alternate compact-supporting head arrangement which permits experimental determination of a slow strain rate tensile strength measurement of a compact, which tensile strength measurement and slow strain rate hardness measurement are used for determining the best case bonding index. This tensile strength measurement is also used for determining the worst case bonding index.

Other objects and advantages of the apparatus according to the present invention will be apparent to persons familiar with arrangements of this general type upon reading the following specification and inspecting the accompanying drawings.

Certain terminology will be used in the following description for convenience in reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the apparatus and designated parts thereof. Said terminology will include the words specifically mentioned, derivatives thereof, and words of similar import.

DETAILED DESCRIPTION

Figure 1:
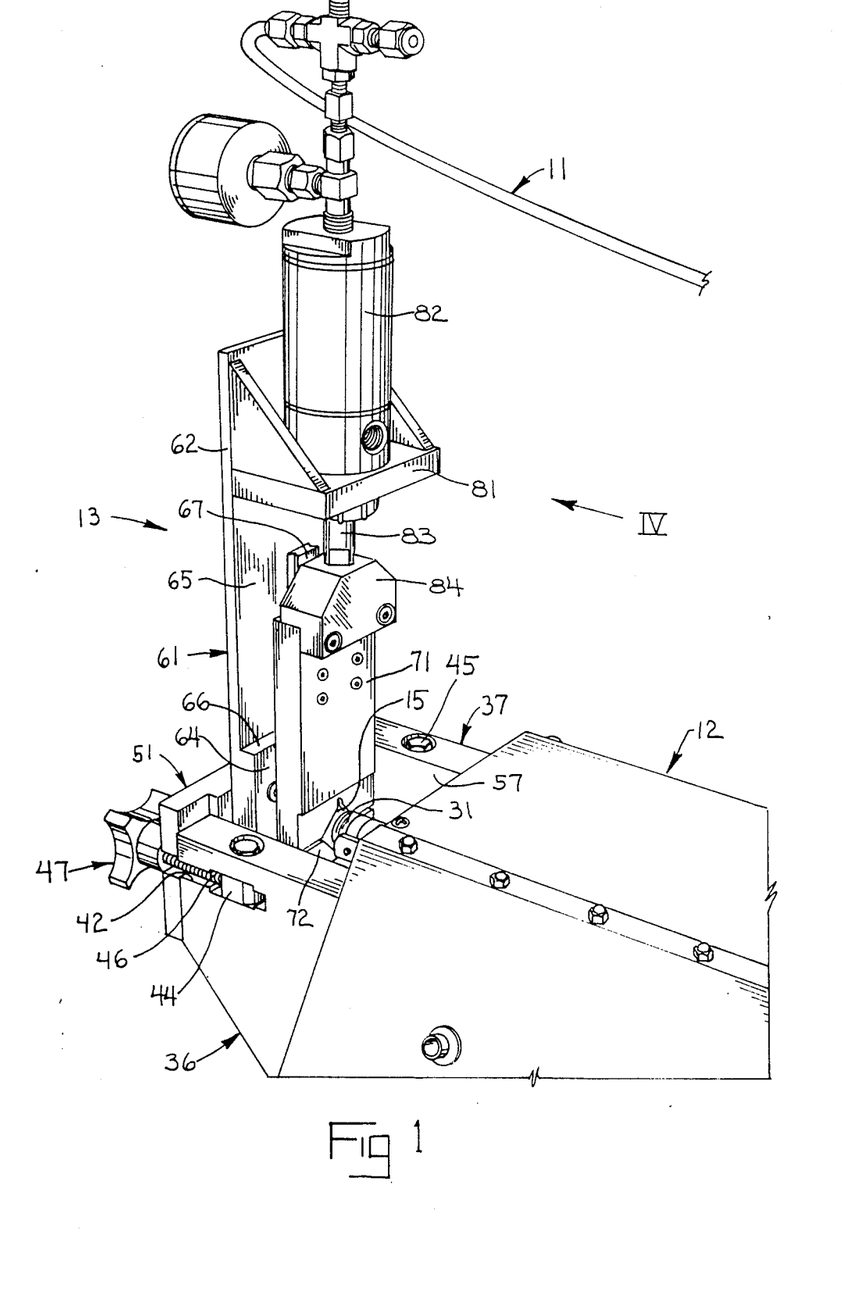
FIG. 1 is a fragmentary perspective view of a slow strain rate shear strength tester having a compact supporting head arrangement mounted thereon for permitting determination of slow strain rate hardness of a test compact.
Figure 2:
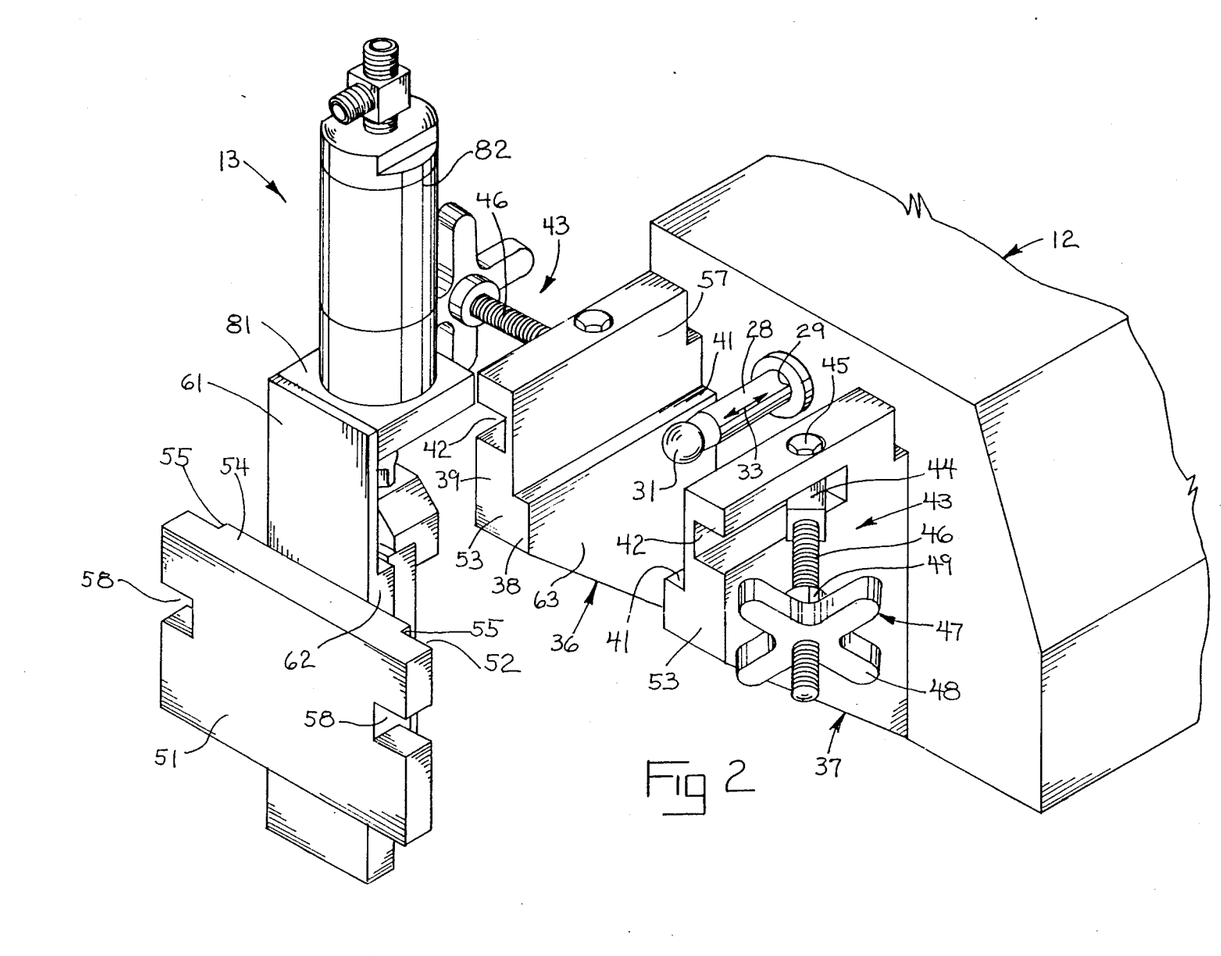
FIG. 2 is a fragmentary perspective view showing, in an exploded or separated condition, the head arrangement and its mounting cooperation with the tester.
Figure 3:
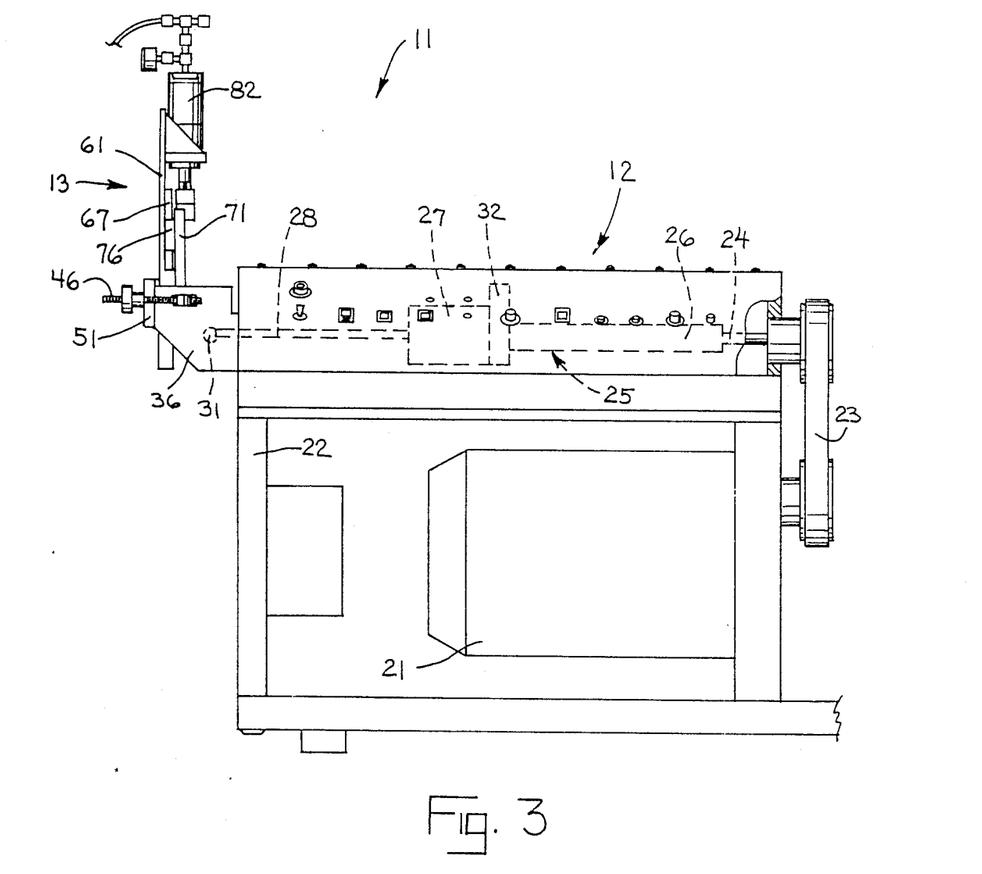
FIG. 3 is a side view of the tester having the head arrangement mounted thereon.

Referring to the drawings, and specifically FIGS. 1-3, there is illustrated a slow strain rate testing apparatus 11 according to the present invention. This apparatus includes a press or ram arrangement 12 which removably mounts thereon a head arrangement 13. This head arrangement 13 is intended for permitting slow strain rate hardness testing. Alternatively, the head arrangement 13 can be removed from the ram arrangement 12 and replaced by an alternate head arrangement 14 (FIGS. 7 and 8), the latter being capable of testing slow strain rate tensile strength. Each of these head arrangements 13 and 14 is adapted to support a tablet or compact 15 (FIGS. 1 and 4), which compact is a rather large block-like member compressed of pharmaceutical powders or particulate material, such compact preferably being created by means of a press as illustrated in copending U.S. patent application Ser. No. 07/187,569, as filed on Apr. 28, 1988, now U.S. Pat. No. 4,880,373.

The ram arrangement 12 includes a reversible variable-speed drive motor 21 which is mounted on the frame or housing 22, and which drives a belt-pulley drive train 23 for effecting rotation of a threaded drive shaft 24. This latter drive shaft 24 is disposed so that its rotational axis extends generally horizontally of the housing, and it effects linear reciprocal movement of a ram assembly 25. This ram assembly 25 includes an internally threaded sleeve 26 which is engaged with the drive shaft 24. Sleeve 26 has one end thereof coupled to a conventional strain gauge transducer 27, and the latter in turn is coupled to the rearward end of a cylindrical ram 28. This ram slidably projects outwardly through an opening 29 formed in the end wall of the housing, and is provided with a compression member (i.e. an indenter) 31 removably mounted on the free end thereof, which compression member 31 in the embodiment illustrated by FIGS. 1-6 comprises a steel ball. The sleeve 26 has a bracket 32 fixed thereto, the latter having sidewardly projecting parts which are slidably guided on a pair of elongate stationary guide rods (not shown) which are disposed in generally parallel relationship to and on opposite sides of the drive shaft. By this arrangement, rotation of the threaded shaft 24 effects linear displacement of the ram assembly 25 so that the cylindrical ram 28 can be either advanced outwardly or inwardly as indicated by the arrow 33 in FIG. 2, depending upon the direction of rotation of the drive motor 21. The transducer 27 is connected to a conventional indicator, preferably a computerized indicator, to permit exact measurement of the compression forces and time to thereby permit an accurate strain measurement.

The overall structural and functional relationships of the ram arrangement 12 are similar to those explained in greater detail in U.S. Pat. No. 4,542,646, as owned by the Assignee hereof, and the disclosure of this latter patent is incorporated herein by reference.

To permit the head arrangement 13 to be easily mounted on or removed from the ram arrangement 12, the ram arrangement includes a mounting means which, as illustrated by FIG. 2, includes a pair of sidewardly spaced support brackets 36 and 37 which project outwardly in a horizontally cantilevered relationship from one end of the housing 22. These brackets 36 and 37 are uniformly sidewardly spaced apart on opposite sides of the ram 28 so that the latter is disposed midway therebetween. Brackets 36 and 37 are identical except for being mirror images of one another.

Each bracket 36, 37 is generally L-shaped in transverse vertical cross section and includes a generally inwardly projecting base leg 38 joined to an upwardly projecting top or vertical leg 39. This construction results in the base leg 38 defining, on the upper surface thereof, a shoulder or step 41 which functions as an elongate guide surface. The guide surfaces 41 as defined on the brackets 36, 37 are disposed generally within a horizontal plane, and each surface 41 is elongate in a direction generally parallel with the longitudinal axis of the ram 28.

The upright leg 39 of each bracket 36, 37 has an elongate slot 42 which opens horizontally inwardly from the free end of the respective bracket. The slot 42 is spaced upwardly from but extends generally parallel to the respectively adjacent guide surface 41.

Each bracket 36, 37 has a clamping arrangement 43 movably supported thereon and disposed for clamping engagement with the head arrangements 13 or 14, as explained hereinafter. The clamping arrangement 43 includes a hinge block 44 which is sized so as to be movably positioned within the respective slot 42. This hinge block 44 at its inner end is coupled to the bracket by a vertically extending hinge element 45, such as a threaded fastener, which hinge element defines a generally vertically extending hinge axis for permitting horizontal swinging of the hinge block 44. This latter block 44 has an elongate threaded shaft 46 fixed thereto and extending outwardly therefrom generally along a radial direction relative to the hinge axis defined by member 45. A clamping member 47 is rotatably threadably engaged on the threaded shaft 46. This clamping member 47 has a gripping part 48 which effectively functions as a gripping wheel for permitting manual grasping thereof, and this gripping part is fixedly and integrally joined to a cylindrical clamping part 49.

Considering now the hardness-testing head arrangement 13, the latter includes a generally vertically oriented mounting plate 51 which is of generally rectangular configuration and has, adjacent opposite vertical edges thereof, inner surfaces 52 which are adapted to directly abut against the outer end surfaces 53 of the brackets 36, 37. The mounting plate 51 has a generally rectangular-shaped guide part 54 which projects inwardly from the inner surface thereof, which guide part is spaced inwardly and upwardly from the respective side and bottom edges of the mounting plate. This guide part 54 has generally parallel vertically extending side guide surfaces 55, and a generally horizontally extending bottom guide surface 56. The side guide surfaces 55 are horizontally spaced apart by a dimension which equals or preferably is slightly smaller than the horizontal spacing between the opposed side surfaces 57 formed on the upright legs 39 of the brackets, whereby the guide part 54 can hence be snugly slidably guided between the upright legs 39. When so positioned, the bottom guide surface 56 on the guide part 54 is disposed for abutting engagement with the guide surfaces 41. This guide part 54 hence enables the mounting plate 51, and in fact enables to complete head arrangement 13, to be precisely positioned and stationarily seated on the outer ends of the brackets 36, 37 so as to effectively close off the outer end of the open region between the brackets.

The mounting plate 51 also has small slots 58 opening inwardly a limited extent from each of the vertical side edges thereof, which slots 58 have a vertical dimension which only slightly exceeds the diameter of the threaded shaft 46 associated with the clamping mechanism so as to permit the threaded shaft to move sidewardly into and project through the respective slot 58.

The head arrangement 13 also includes a vertically elongate support plate 61 which is fixedly secured to the mounting plate 51 and projects both vertically upwardly and downwardly therefrom. This support plate 61 is fixedly secured to and projects inwardly from the guide part 54, and the support plate 61 is of reduced horizontal width as defined between opposed vertically extending side surfaces 62. The horizontal dimension between these side surfaces 62 is equal to or only slightly smaller than the horizontal spacing between the opposed side surfaces 63 defined on the base legs 38 of the brackets so that the support plate 61 can be moved slidably inwardly between these opposed side surfaces 63 so as to be snugly confined therebetween.

The vertical support plate 61 includes a vertically-oriented lower plate part 64 which is disposed generally between the support brackets 36, 37, and a vertically-oriented upper plate part 65 which is integral with the lower plate part but of reduced plate thickness so as to result in a step or shoulder 66 at the interface therebetween. This upper plate part 65 has a vertically elongate rib or guideway 67 fixed thereto and projecting vertically centrally thereof, which guideway projects upwardly from the shoulder 66 through a substantial vertical extent. Guideway 67 has vertically elongate and generally parallel guide grooves 68 formed in the opposite sides thereof.

The lower plate part 64 also has a platelike guideway 69 which projects forwardly therefrom and extends vertically downwardly along the inner face thereof.

The support plate 61 mounts thereon upper and lower tablet holders 71 and 72, respectively, the latter being supported for relative vertical displacement to permit a known tablet or compact 15 to be held therebetween. In the illustrated embodiment, the lower tablet holder 72 is fixedly secured, as by means of screws 73, to the lower portion of the lower plate part 64 and projects outwardly therefrom into the region between the brackets 36 and 37. This lower tablet holder 72 has an upper edge which is spaced slightly below a horizontal plane containing the longitudinal axis of the cylindrical ram 28, and a generally V-shaped notch 74 opens downwardly from the upper edge of the lower tablet holder 72. The side walls of this notch 74 define a generally 90° angle therebetween so as to accommodate one corner of a conventional tablet 15.

Figure 6:
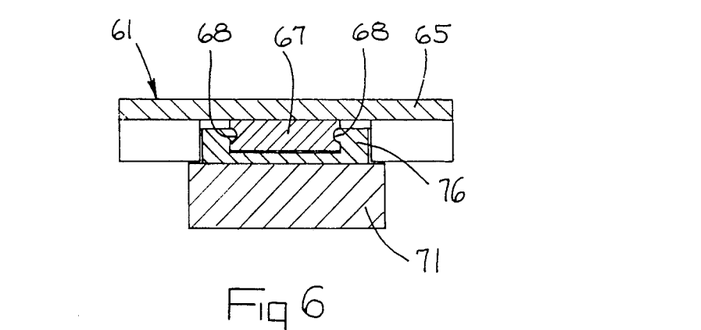

The upper tablet holder 71 is supported for vertical slidable displacement on the support plate 61, and for this purpose the upper portion of tablet holder 71 has a vertically-elongate slide member 76 fixedly secured to the rear surface thereof. This slide member 76 is of a generally channel or U-shaped configuration so as to be confined for vertical slidable movement along the guideway 67 as illustrated by FIG. 6. This upper tool holder 71, however, adjacent the lower portion thereof is also provided with a channellike guide recess 77 formed in the rear surface thereof, which latter recess 77 closely vertically slidably accommodates the platelike guideway 69. Hence, the lower end of the upper table holder 71 is effectively directly slidably supported on the plate part 64. The lower edge of this upper tablet holder also has a generally V-shaped notch 78 formed therein and opening upwardly therefrom, which notch also defines an included angle of 90° so that the notches 74 and 78 are substantially identical but disposed in directly opposed relationship to one another to hence confine a compact 15 therebetween when the latter is oriented with its diagonal extending generally vertically. When in the closed and compact-supporting position illustrated by FIG. 4, the center of the compact 15 is disposed substantially on and aligned with the horizontal longitudinal axis of the cylindrical ram 28 so that the compression ball 31 will effectively contact the front surface of the compact 15 substantially at the center thereof.

To effect vertical displacement of the upper tablet holder 71, the support plate 61 adjacent the upper extremity thereof mounts thereon a horizontally projecting top support plate 81. This latter plate 81 in turn mounts a driver, such as a conventional double-acting pneumatic cylinder 82. The reciprocal piston rod 83 of this drive cylinder 82 projects vertically downwardly and has a coupling plate 84 fixed to the lower free end thereof, which coupling plate 84 in turn is fixedly secured to the upper end of the tablet holder 71.

OPERATION

The operation of the apparatus illustrated by FIGS. 1–6 will be briefly described.

Assuming that the head arrangement 13 is initially disassembled substantially as illustrated by FIG. 2, then the head arrangement (which can be readily handled since it is basically a unitary structure) is disposed adjacent the free ends of the support brackets 36 and 37, and is then slidably moved horizontally inwardly so as to be properly seated on and between the support brackets. More specifically, the support plate 61 is moved inwardly so as to be snugly disposed between the opposed side surfaces 63 of the brackets, and the guide part 54 is moved inwardly so as to be snugly disposed between the opposed side surfaces 57 of the brackets. At the same time, the head arrangement is vertically oriented and precisely positioned by ensuring that the bottom guide surface 56 is snugly seated on the guide surfaces 41 of the brackets.

Figure 4:
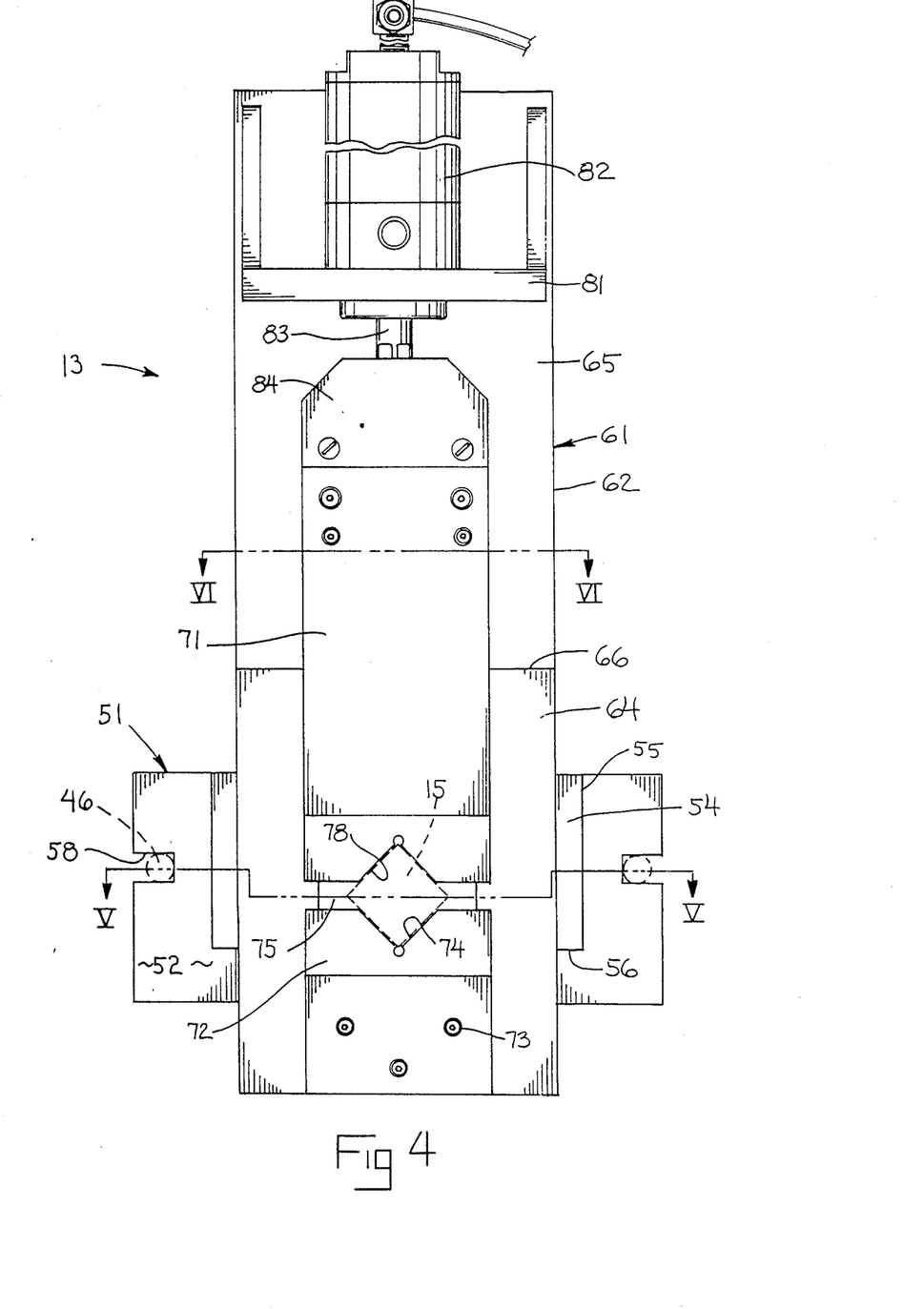
FIG. 4 is an end elevational view of the head arrangement as taken substantially in the direction of arrow IV in FIG. 1.
Figure 5:
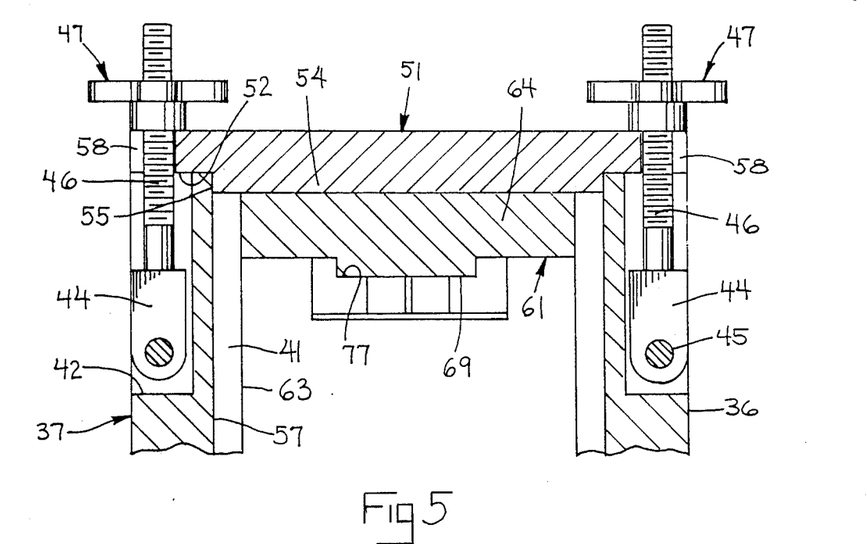
FIGS. 5 and 6 are sectional views taken along lines V—V and VI—VI, respectively, in FIG. 4.

After the head arrangement has been properly positioned on the brackets, then the clamping arrangements 43 are swung inwardly from the position of FIG. 2 until the threaded shafts 46 extend through the slots 58 as illustrated by FIGS. 4 and 5. The manual clamping members 47 are then manually rotated on the threaded shafts until the cylindrical parts 49 thereof abut the outer surface of the mounting plate 51 so as to effect tight clamping of the mounting plate against the outer end surfaces 53 of the support brackets 36 and 37.

Assuming that the upper tablet holder 71 is in its raised position, then a tablet or compact 15 is positioned within the lower notch 74, and drive cylinder 82 is energized to lower the upper tablet holder 71 until the upper portion of the tablet is confined within the notch 78. A predetermined pressure is preferably continually maintained on the cylinder 82 so as to hence maintain a predetermined downward holding force on the tablet 15 during the subsequent portions of the test. Due to the diagonal orientation of the tablet relative to the vertical holding force created by the driving cylinder 82, the holding force is compressively applied substantially uniformly to each of the tablet sides.

Thereafter the ram assembly 25 is energized and advanced outwardly (leftwardly in FIGS. 1–3) until the compression ball 31 substantially contacts the front face of the tablet. At that point the speed advance of the ram is significantly reduced and the ram continues to advance outwardly until it has advanced enough to produce the desired dent size, e.g. 3 mm. chordal radius, in the front surface of the compact. At this point the ram is stopped and held stationary for a substantial period of time, the desired dwell time being, for example, 30 minutes. Throughout this compression stage, the compression force is measured by the transducer 27 and hence can be accurately measured and plotted by appropriate visual indicating devices connected thereto. This permits the properties of the tablet to be accurately measured. After the selected dwell time has elapsed, then the drive to the ram is reversed and the ram 28 is rapidly retracted to its original position. The drive cylinder 82 is then energized upwardly so that the upper holder 71 is raised, whereupon the compact 15 can be readily manually removed, and a further compact inserted into the lower notch 74 so as to permit a further test to be carried out if desired.

With the head arrangement 13 as described above, the cooperation of the plates 51 and 61 with the opposed cantilevered brackets 36 and 37 results in a very strong and rigid arrangement inasmuch as the plates 61 and 51 effectively rigidly join the outer free ends of the brackets 36 and 37, and since the latter are rigidly joined at their other ends by the housing 22, there is thus provided a very rigid and yet precise framelike structure, the latter being in surrounding relationship to a vertically-oriented space in which the ram 28 and tablet holders 71-72 are accommodated but yet are readily accessible. In addition, the compression forces imposed by the ram onto the tablet are transmitted directly through the tablet onto the front surface 75 defined on the plate part 64, which forces in turn are transmitted directly therethrough to the mounting plate 51, whereby the forces are then resisted by the clamping mechanism 43. These latter mechanisms in effect transmit the ram forces back to the brackets 36 and 37.

When removal of the head arrangement 13 is desired, same can be quickly and simply accomplished merely by loosening the two clamping members 47 by effecting manual rotation thereof, and then swinging the two clamping shafts 46 outwardly substantially as illustrated by FIG. 2, following which the complete head arrangement 13 can be manually gripped and then slidably moved outwardly to wholly disengage it from the support brackets.

ALTERNATE STRUCTURE

Figure 7:
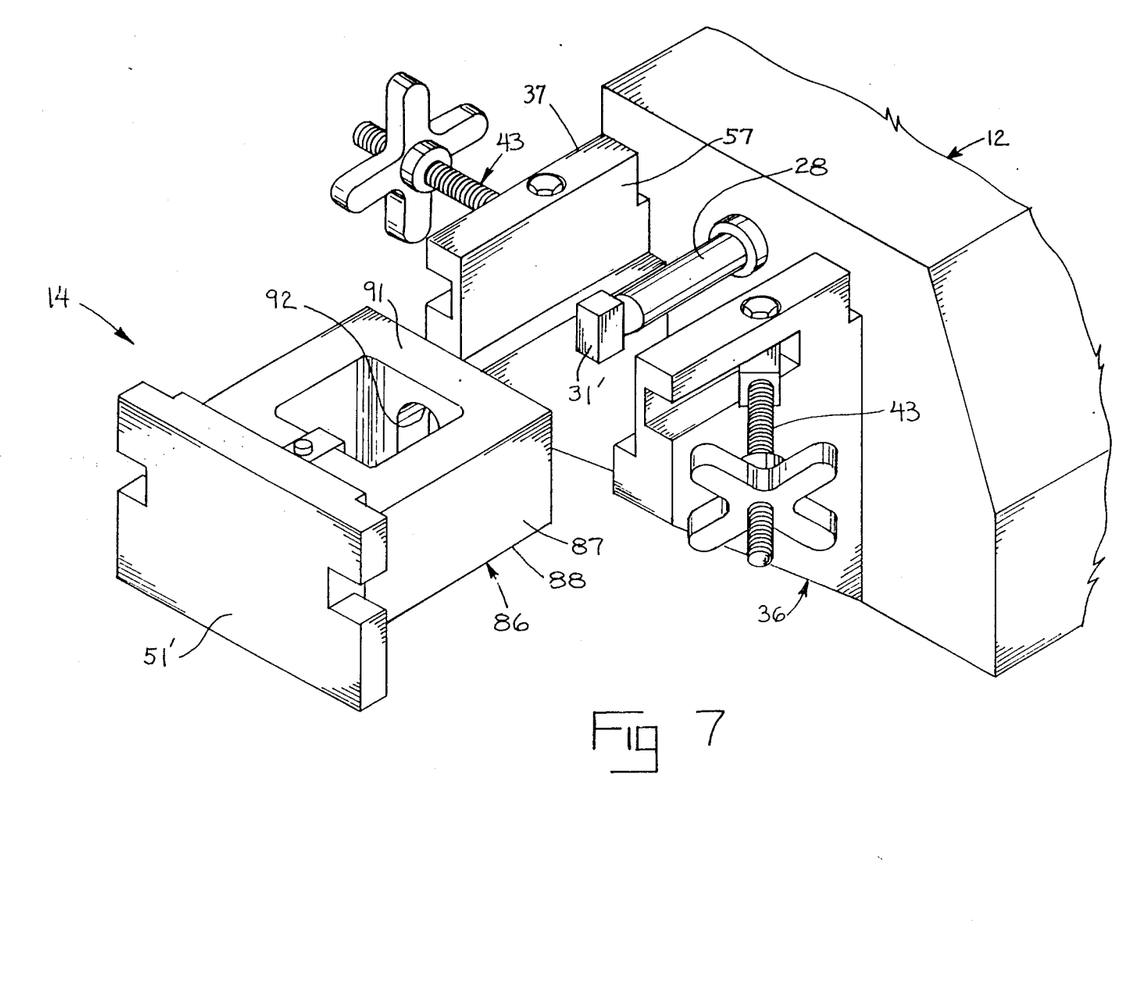
FIG. 7 is a view similar to FIG. 2 but showing an alternate head arrangement for permitting testing of tensile strength.
Figure 8:
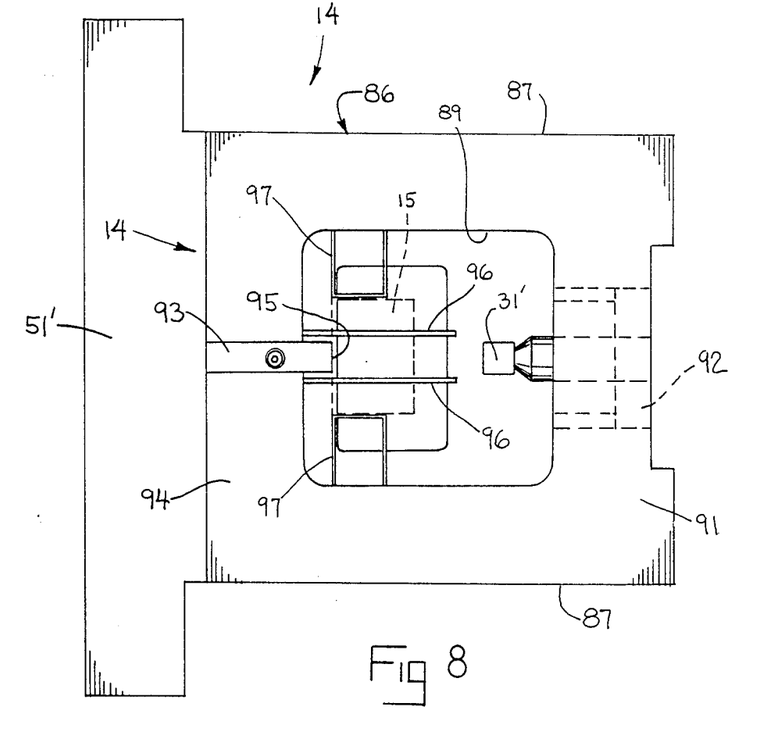
FIG. 8 is a top view of the alternate head arrangement shown in FIG. 7.

Referencing now FIGS. 7 and 8, there is illustrated the alternate head arrangement 14 which can be mounted on the support brackets 36 and 37, which head arrangement 14 permits testing for determining tensile strength of a tablet or compact 15. In this variation, the head arrangement 14 includes a mounting plate 51' which is identical to the mounting plate 51 described above and which cooperates with the brackets 36 and 37 in the same manner. This mounting plate 51' has, fixedly attached to the inner surface thereof, a rigid support frame 86 which is a generally hollow ringlike frame of generally square configuration. This support frame 86 has one side wall thereof abutted against the inner surface of the mounting plate 51' so as to be fixedly secured thereto, whereby the support frame 86 projects horizontally in a generally cantilevered relationship from the mounting plate 51'. The support frame 86 has generally opposite parallel side walls 87 which are adapted to be snugly slidably accommodated between the opposed side walls 57 of the brackets. The frame 86 also has a bottom surface 88 which slidably engages the bracket guide surfaces 41 so that the frame 86 can be slidably supported thereon. The guide frame 86 has a generally rectangular cross-section opening 89 extending vertically therethrough, which opening 89 is of reduced cross section as it projects downwardly. The front wall 91 of the frame 86 has an opening 92 extending therethrough for communication with the opening 89, whereby this opening 92 permits the ram 28 to project therethrough. The ram 28, in this variation, preferably has a modified compression element 31', such as a rectangular block, secured to the free end thereof.

The support frame 86 has a platen or anvil 93 which is fixed to and projects inwardly from the front frame wall 94 which platen 93 defines thereon an abutment or anvil surface 95 which is adapted to abut the rear side of the tablet 15. This anvil surface 95 is disposed so that the center thereof is substantially aligned with the axis of the ram, and is sized identical to the front surface of compression element 31'. A pair of tablet support blades 96 are fixed to and project in cantilevered fashion outwardly from the wall 94 in straddling relationship to the platen. Blades 96 straddle the element 31' when the latter is in its advance position. These tablet support blades 96 are generally parallel with one another and comprise vertical plates which are horizontally thin so as to have only small upper edges which supportingly engage the bottom surface of the tablet 15. These blades 96 support the tablet so that the center of the front face of the tablet is substantially aligned with the longitudinal axis of the ram. Spring clips 97 projects outwardly from opposite sides of the frame 86 so as to resiliently engage opposite sides of the tablet to assist in holding it in position when supported on the blades 96.

This alternate head arrangement 14 can be readily mounted on or removed from the support brackets 36 and 37 in substantially the same manner as explained above relative to the head arrangement 13.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A slow strain rate compression tester for measuring a physical characteristic of a large blocklike tablet of compressed particulate material, such as for pharmaceutical applications, said tester comprising: a pressing arrangement including a housing having a generally vertical end wall, a drive motor, and a ram assembly coupled to and driven by said drive motor for linear reciprocating movement relative to said housing along a substantially horizontal movement axis, said ram assembly including a linearly reciprocal ram member which is elongate along said horizontal movement axis and which slidably projects outwardly beyond the end wall of said housing, said ram member having a tablet compression element mounted on a free outer end thereof;

first and second support bracket means fixedly mounted on the end wall of said housing and projecting outwardly therefrom in generally cantilevered relation, said first and second bracket means being sidewardly spaced apart and defining a vertically open region therebetween, said ram member being positioned centrally within said region with said first and second bracket means being disposed substantially equally horizontally spaced from said ram member on opposite sides thereof;

each of said bracket means defining thereon an upper inner side surface and a lower inner side surface which are sidewardly spaced apart and are joined together by a generally upwardly facing and substantially horizontally extending steplike surface, the upper inner side surfaces on said first and second bracket means being disposed in directly opposed and parallel relationship, the lower inner side surfaces of said first and second bracket means being disposed in directly opposed and parallel relationship, the transverse horizontal spacing between the opposed lower side surfaces being less than the transverse horizontal spacing between the opposed upper side surfaces;

said first and second bracket means defining thereon outer end surfaces which are sidewardly spaced apart and which are disposed within a generally common vertical plane;

manually-operable clamping means mounted on each of said bracket means and including an elongate member which is coupled to the respective bracket means and which projects outwardly a significant extent beyond the end surface and which mounts thereon a manually movable clamping member; and a tablet-supporting head assembly removably mounted on said first and second support bracket means and fixedly secured to said bracket means by said clamping means;

said head assembly including a generally vertically oriented mounting plate extending horizontally between said first and second bracket means and having opposite vertically-extending edge portions which overlap and abut the end surfaces of said first and second bracket means, the edge portions having openings extending therethrough for accommodating the elongate members of the clamping means to permit the mounting plate to be rigidly and fixedly clamped to the end surfaces of the first and second bracket means to close off the outer end of said open region whereby said mounting plate is spaced horizontally outwardly from the end wall of said housing, said mounting plate having guide means fixedly and integrally associated therewith and projecting inwardly therefrom for slidable and abutting engagement with the opposed upper inner surfaces and the steplike surfaces defined on said first and second bracket means;

said head assembly also including tablet support means mounted to said mounting plate and projecting inwardly therefrom into the region between said first and second bracket means, said tablet support means having a pair of tablet engaging members for supporting a tablet so that parallel side faces of the tablet are vertically oriented with one said side face abutting a flat support surface defined on the tablet support means, the other side face being disposed substantially in opposed relation to the tablet compression element and substantially aligned with the horizontal motion axis so as to be contacted by the tablet compression element during extension of the ram member.

2. A tester according to claim 1, wherein said tablet support means includes a vertically elongate support plate which is fixed to an inner surface of said mounting plate and which projects inwardly therefrom into the region between said first and second bracket means adjacent the outer ends thereof, said vertically elongate support plate projecting vertically upwardly a substantial extent above said bracket means, said pair of tablet engaging members comprising upper and lower tablet holders which cooperate to define therebetween a generally square tablet-receiving opening oriented such that a diagonal of the square opening is oriented vertically, said lower tablet holder being fixedly secured to a lower portion of said support plate and having an upper edge in which is defined a generally upwardly-opening V-shaped notch for accommodating a lower corner portion of the tablet, said upper tablet holder being vertically slidably supported on said support plate and having a lower edge which defines therein a downwardly-opening V-shaped notch for accommodating an upper corner portion of the tablet, said notches directly vertically disposed one over the other for defining said square tablet-accommodating opening when the upper tablet holder is in a lowermost position, and reciprocal drive means mounted on an upper portion of said support plate and coupled to said upper tablet holder for effecting linear reciprocal movement thereof vertically between said lowermost position and an uppermost position which permits insertion or removal of the tablet from the notch in the lower tablet holder.

3. A tester according to claim 2, wherein the elongate member as associated with each bracket means is hingedly mounted on the bracket means adjacent the inner end thereof by a hinge which permits the elongate member to be swingable generally horizontally outwardly away from the bracket means to permit release of the mounting plate, the opening as defined in each edge portion of the mounting plate comprising a slot which opens sidewardly through the side edge of the mounting plate so that the elongate member can be swung about its pivot axis horizontally into and out of the slot, said elongate member being threaded at least adjacent the outer free end thereof, and said clamping member being a manually-engageable clamping member which is rotatably threadedly supported on said elongate member adjacent the outer end thereof and adapted for clamping engagement with an outer surface of the mounting plate.

4. A tester according to claim 3, wherein said tablet compression element comprises a steel ball.

5. A tester according to claim 4, wherein said reciprocal drive means comprises a fluid pressure cylinder.

6. A tester according to claim 1, wherein said tablet support means includes a rigid support ring having a vertical opening therethrough, the support ring being fixed to said mounting plate and projecting inwardly for snug sideward confinement between said first and second bracket means, said tablet engaging members supporting the tablet within said vertical opening, 7. A slow strain rate compression tester for measuring a physical characteristic of a large blocklike tablet of compressed particulate material, such as for pharmaceutical applications, said tester comprising:

a pressing arrangement including a housing having a generally vertical end wall, a drive motor, and a ram assembly coupled to and driven by said drive motor for linear reciprocating movement relative to said housing along a substantially horizontal movement axis, said ram assembly including a linearly reciprocal ram member which is elongate along said horizontal movement axis and which slidably projects outwardly beyond the end wall of said housing, said ram member having a tablet compression element mounted on a free outer end thereof;

first and second support bracket means fixedly mounted on the end wall of said housing and projecting outwardly therefrom in generally cantilevered relation, said first and second bracket means being sidewardly spaced apart and defining a vertically open region therebetween, said ram member being positioned centrally within said region with said first and second bracket means being disposed substantially equally horizontally spaced from said ram member on opposite sides thereof;

said first and second bracket means defining thereon outwardly-facing end surfaces which are sidewardly spaced apart and which are disposed within a generally common vertical plane;

a tablet-supporting head assembly fixedly but removably mounted on said first and second support bracket means;

manually-operable clamping means coacting between said head assembly and each said bracket means for fixedly but removably securing said head assembly to said bracket means;

said head assembly including a generally vertically oriented mounting plate extending horizontally between said first and second bracket means and having opposite vertically-extending edge portions which overlap and abut the outwardly-facing end surfaces of said first and second bracket means, said mounting plate having guide means fixedly associated therewith and projecting inwardly therefrom for slidable engagement with opposed inner surfaces on said first and second bracket means;

said head assembly also including tablet support means mounted to said mounting plate and projecting inwardly therefrom into the region between said first and second bracket means, said tablet support means having a pair of tablet engaging members for supporting a tablet so that parallel side faces of the tablet are vertically oriented with one said side face abutting a flat support surface defined on the tablet support means, the other side face being disposed substantially in opposed relation to the tablet compression element and substantially aligned with the horizontal motion axis so as to be contacted by the tablet compression element during extension of the ram member.

* * * * *